US009187416B2

(12) United States Patent
Qiu et al.

(10) Patent No.: US 9,187,416 B2
(45) Date of Patent: *Nov. 17, 2015

(54) PARTIALLY FLUORINATED SULFINIC ACID MONOMERS AND THEIR SALTS

(75) Inventors: Zai-Ming Qiu, Woodbury, MN (US); Gregg D. Dahlke, St. Paul, MN (US); Tatsuo Fukushi, Woodbury, MN (US); Werner M. Grootaert, Oakdale, MN (US); Miguel A. Guerra, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/885,202

(22) PCT Filed: Dec. 9, 2011

(86) PCT No.: PCT/US2011/064154

§ 371 (c)(1),
(2), (4) Date: May 14, 2013

(87) PCT Pub. No.: WO2012/082551

PCT Pub. Date: Jun. 21, 2012

(65) Prior Publication Data

US 2013/0253220 A1  Sep. 26, 2013

Related U.S. Application Data

(60) Provisional application No. 61/424,109, filed on Dec. 17, 2010.

(51) Int. Cl.
*C07C 313/04* (2006.01)
*C07C 17/275* (2006.01)
*C07C 303/22* (2006.01)
*C08F 214/18* (2006.01)

(52) U.S. Cl.
CPC ............ *C07C 313/04* (2013.01); *C07C 17/275* (2013.01); *C07C 303/22* (2013.01); *C08F 214/186* (2013.01)

(58) Field of Classification Search
None
See application file for complete search history.

(56) References Cited

U.S. PATENT DOCUMENTS

| 2,950,317 | A | 8/1960 | Brown |
| 4,332,665 | A | 6/1982 | Kimoto |
| 4,544,458 | A | 10/1985 | Grot |
| 5,285,002 | A | 2/1994 | Grootaert |
| 5,639,837 | A | 6/1997 | Farnham |
| 6,191,231 | B1 | 2/2001 | Drysdale et al. |
| 6,462,228 | B1 | 10/2002 | Dams |
| 2004/0039142 | A1 | 2/2004 | Yang |
| 2004/0192868 | A1 | 9/2004 | Kaspar |
| 2010/0035185 | A1 | 2/2010 | Hagiwara et al. |

FOREIGN PATENT DOCUMENTS

| CN | 1072407 | | 5/1993 |
| CN | 1221735 | | 7/1997 |
| CN | 1752059 | A | 3/2006 |
| EP | 0 289 869 | | 11/1988 |
| JP | 2001-509206 | | 7/2001 |
| JP | 2006-131588 | | 5/2006 |
| JP | 2008-127317 | * | 6/2008 |
| JP | 2009/3727 | | 6/2009 |
| WO | WO 97/02300 | | 1/1997 |
| WO | 0077057 | * | 12/2000 |
| WO | WO 2008-083201 | | 7/2008 |
| WO | 2009/078335 | | 6/2009 |
| WO | WO 2012-082454 | | 6/2012 |
| WO | WO 2012-082546 | | 6/2012 |
| WO | WO 2012-082695 | | 6/2012 |
| WO | WO 2012-082703 | | 6/2012 |

OTHER PUBLICATIONS

Database Caplus Chemical Abstracts Service, Columbus, Ohio, US; Database Accession No. 1992:427945, Abstract of JP 04011608 "Polymeric protonic conductors as electrolytes for fuel cells", Hado et al. Nov. 6, 1992.*
Database Caplus Chemical Abstracts Service, Columbus, Ohio, US; Database Accession No. 2003:1006939, Abstract of Sugiyama et al., Daikin Industries, Ltd., Japan, WO 2003106407, Dec. 24, 2033.*
Bargigia, "Perfluoro-w-Iodo-3-Oxaalkanesulfonyl Fluorides as Intermediates for Surfactants and Vinyl Compounds (*)", J.Fluorine Chem.,1982, vol. 19, pp. 403-410.
Chen, "Iodofluoroalkylsulfonyl Fluorides—Synthesis and Conversion to New Derivatives", J. Fluorine Chem., 1989, vol. 43, pp. 329-347.
Fan-Hong, "Studies on Sulfinatodehalogenation. XXIX. The Sulfinatodehalogenation of Primary Polyfluoroalkyl Iodides and Bromides by Sodium Disulfite", Journal of Fluorine Chemistry, 1994, vol. 67, pp. 233-234.
Hu, "Reaction of Perfluoroalkanesulfinates with Allyl and Propargyl Halides. A Convenient Synthesis of 3-(Perfluoroalkyl)prop-l-enes and 3-( Perfluoroalkyl)allenes", J. Org. Chem., 1991, vol. 56, pp. 2801-2804.

(Continued)

Primary Examiner — Karl J Puttlitz
(74) Attorney, Agent, or Firm — Julie Lapos-Kuchar

(57) ABSTRACT

Described herein is a composition according to formula I or its precursor, formula II: $CX_1X_3=CX_2-(R_1)_p-CZ1Z2-SO_2M$ (I) wherein $X_1$, $X_2$, and $X_3$ are independently selected from H, F, Cl, Br, I, $CF_3$ and $CH_3$, and wherein at least one of $X_1$, $X_2$, or $X_3$ is a H; $R_1$ is a linking group; Z1 and Z2 are independently selected from F, Cl, Br, I, $CF_3$, and a perfluoroalkyl group; p is 0 or 1; and M is a cation; and $CX_4X_1X_3-CX_5X_2-(R_1)_p-CZ1Z2-SO_2M$ (II) wherein $X_1$, $X_2$, and $X_3$ are independently selected from H, F, Cl, Br, I, $CF_3$ and $CH_3$, wherein at least one of $X_1$, $X_2$, or $X_3$ is a H, and $X_4$ and $X_5$ are independently selected from H, F, Cl, Br and I; $R_1$ is a linking group; Z1 and Z2 are independently selected from F, Cl, Br, I, $CF_3$, and a perfluoroalkyl group, p is 0 or 1; and M is selected from F, and a cation.

5 Claims, No Drawings

(56) References Cited

OTHER PUBLICATIONS

Hu, "Study on the Sulfinatodehalogenation of $BrCF_2CF_2R$", 1995,vol. 15 No. 5, pp. 472-474.
Huang, "Studies on Sulfinatodehalogenation", Chinese Journal of Chemistry, 1991, vol. 9, pp. 351-359.
Huang, "The Reaction of Perfluoroalkanesulfinates—The Study on Perfluoroalkanesulfinates as Perfluoroalkylation Reagents"., Acta Chimica Sinica (English Edition), 1989, No. 2, pp. 190-192.
Huang, "The Reaction of Perfluoroalkanesulfinates IV. Perfluoroalkyl Radical Addition to Olefins Initiated by Single Electron Oxidation of Perfluoroalkanesulfinate", Chinese J. Chem., 1990, vol. 4, pp. 362-369.
Manseri, "Synthesis of Telechelic Dienes From Fluorinated α,w-Diiodoalkanes.Part I. Divinyl and Diallyl Derivatives From Model I $(C_2F_4)_nI$ Compounds", J. Fluorine Chem., 1995, vol. 73, pp. 151-158.
Su, "Studies on fluoroalkylation and fluoroalkoxylation 32. the addition reactions of difluoroiodomethane sulfonly fluoride with olefine in the presence of copper-coexistence of radical and carbene processes induced by electron transfer", Acta Chimica Sinica (Chinese Edition), 1990, vol. 48, Issue 6, pp. 596-601.
Yang, "Copolymerization of Ethylene,Tetrafluoroethylene, and an Olefin-Containing Fluorosulfonyl Fluoride: Synthesis of High-Proton-Conductive Membranes for Fuel-Cell Applications", Angew Chen. Int., 2005, vol. 44, Issue 4, pp. 564-567.
Ya-Xiong, "Perfluoro- and Polyfluorosulfonic Acids VII. The Preparation of Olefins Containing Fluorosulfonyl Group", Acta Chimica Sinica (Chinese Edition), 1982, vol. 40, No. 10, pp. 904-912.
Yuan, "Sulfite Radical Anion and Sodium Perfluoroalkane Sulfinate Initiated Addition of Perfluoroalkyl Iodide on Double Bond", Acta Chimica Sinica (Chinese Edition), 1988, vol. 46, pp. 669-673.

International Search Report for PCT International Application No. PCT/US2011/064154, mailed on Aug. 9, 2012, 5 pages.
Chemical Abstracts Service, Columbus, Ohio, US; Zhang, Yongming et al. "Proton exchange membrane and preparation method and use thereof", XP002732093.
Chemical Abstracts Service, Columbus, Ohio, US; Zhang, Yongming et al. "Proton exchange membrane, its preparation method and application", XP002732094.
Chemical Abstracts Service, Columbus, Ohio, US; Zhang, Yongming et al. "Multilayer microporous membrane-reinforced crosslinked doped fluorine-containing ion exchange membrane for fuel cell and its preparation method", XP002732095.
Chemical Abstracts Service, Columbus, Ohio, US; Umemura, Kazuo, et al. "Manufacture of perfluorosulfonic acid copyolyer membranes with good electrochemical properties", XP002732096.
Chemical Abstracts Service, Columbus, Ohio, US; Suzuki, Koji, et al. "Electrolysis of alkali metal chloride for hydroxide preparation", XP002732097.
Chemical Abstracts Service, Columbus, Ohio, US; "Metal carbonyl treatment of F-containing sulfonyl compounds", XP002732098.
Chanda, Manas, and Salil K. Roy. Plastics Technology Handbook, Boca Raton, FL:CRC/Taylor & Francis Group, 2007, ISBN 0-8493-7039-6•.
Huang, Wei Yun and Yuan Xie, "The Reaction of Perfluoroalkanesulfinate with $PCI_3$," *Chinese Chemical Letters*, vol. 1, No. 1, (1990) pp. 27-28.
Yagupolskii, Lev M., et al., A New One-Pot Synthesis of Difluoro(organylsulfinyl)acetic Acid Esters, *Journal of Fluorine Chemistry*, vol. 119 (2003) pp. 59-63.

* cited by examiner

PARTIALLY FLUORINATED SULFINIC ACID MONOMERS AND THEIR SALTS

TECHNICAL FIELD

The present disclosure relates to partially fluorinated sulfinic acids and salts thereof and methods of making.

BACKGROUND

In the polymerization of fluoromonomers, traditionally the monomers are added to a kettle along with an initiator, to initiate the polymerization, as well as a solvent, and in the case of aqueous emulsion polymerization, the polymerization is carried out in water and typically in the presence of an emulsifier in order to stabilize the emulsion.

Fluorinated sulfinic acids and their salts have been used to initiate polymerization. The fluorinated sulfinic acids and their salts have been used along with oxidizing agents during polymerization of fluoromonomers as a means for achieving perfluorinated end groups, which may offer the advantages of more stability, improved performance, etc. by reducing or eliminating the less stable polar end-groups. As disclosed in Grootaert (U.S. Pat. No. 5,285,002), the fluorinated sulfinic acid or salt thereof reacts with an oxidizing agent to generate a fluorinated alkyl radical via electron transfer, which then initiates the polymerization of monomers.

Various papers have described how to prepare fluorinated sulfinic acids or their salts by reduction of sulfonyl fluoride with different reducing agents or by dehalosulfination reaction from fluorinated halides. Examples of different reducing agents used to reduce a sulfonyl fluoride are $NH_2NH_2$ as described in U.S. Pat. No. 2,950,317 (Brown et al.), $M_2SO_3$ and $NaBH_4$ as described in U.S. Pat. No. 5,285,002 (Grootaert), and $K_2SO_3$ as described in U.S. Pat. No. 5,639,837 (Farnham et al.). Examples of a dehalosulfination reaction from fluorinated halides are described by Huang et al. in Journal of Fluorine Chemistry, vol. 23 (1983) p. 193-204 and p. 229-240; by Huang et al. in Chinese Journal of Chemistry, vol. 9 (1991) p. 351-359, and Fan-Hong et al., in Journal of Fluorine Chemistry, vol. 67 (1994) 233-234.

SUMMARY

There is a desire to identify alternative methods for initiating polymerization of fluoromonomers. There is also a desire to identify novel compositions and methods of making, which would enable the ability to change the molecular weight or architecture (e.g., linear or branch) of a polymer. These novel compositions may improve the processing of fluoropolymer polymerization (e.g., by reducing processing step) and/or may improve the finished properties (performance, etc.) of a polymerized fluoropolymer.

In one aspect, a composition according to formula I or its precursor, formula II is described. Where Formula I is:

$$CX_1X_3{=}CX_2{-}(R_1)_p{-}CZ1Z2\text{-}SO_2M \quad (I)$$

wherein $X_1$, $X_2$, and $X_3$ are independently selected from H, F, Cl, Br, I, $CF_3$ and $CH_3$, and wherein at least one of $X_1$, $X_2$, or $X_3$ is a H; $R_1$ is a linking group; Z1 and Z2 are independently selected from F, Cl, Br, and $CF_3$; p is 0 or 1; and M is a cation; and formula II is:

$$CX_4X_1X_3{-}CX_5X_2{-}(R_1)_p{-}CZ1Z2\text{-}SO_2M \quad (II)$$

wherein $X_1$, $X_2$, and $X_3$ are independently selected from H, F, Cl, Br, I, $CF_3$ and $CH_3$, wherein at least one of $X_1$, $X_2$, or $X_3$ is a H, and $X_4$ and $X_5$ are independently selected from H, F, Cl, Br and I; $R_1$ is a linking group; Z1 and Z2 are independently selected from F, Cl, Br, and $CF_3$, p is 0 or 1; and M is selected from F, and a cation.

In another aspect, a method is described comprising (a) reacting a terminal alkene compound with a halofluorosulfonylfluoride to produce a halohydrofluorosulfonylfluoride; (b) dehalohydrogenating the halohydrofluorosulfonylfluoride to produce an alkenefluorosulfonylfluoride; and (c) reducing of the alkenefluorosulfonylfluoride to produce an alkenefluorosulfinic acid or salt.

In yet another aspect, another method is described comprising (a) reacting a terminal alkene compound with a dihalofluorocarbon to produce a haloalkenefluorocarbon halide; (b) sulfinating the haloalkenefluorocarbon halide to produce a haloalkenefluorosulfinic acid or salt; and (c) dehalohydrogenating the haloalkenefluorosulfinic acid or salt to produce an alkenefluorosulfinic acid or salt.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more;

"and/or" is used to indicate one or both stated cases may occur, for example A and/or B includes, (A and B) and (A or B);

"linking group" refers to a divalent linking group. In one embodiment, the linking group includes at least 1 carbon atom (in some embodiments, at least 2, 4, 8, 10, or even 20 carbon atoms). The linking group can be a linear or branched, cyclic or acyclic structure, that may be saturated or unsaturated, substituted or unsubstituted, and optionally contains one or more hetero-atoms selected from the group consisting of sulfur, oxygen, and nitrogen, and/or optionally contains one or more functional groups selected from the group consisting of ester, amide, sulfonamide, carbonyl, carbonate, urethane, urea, and carbamate. In another embodiment, the linking group does not comprise a carbon atom and is a catenary heteroatom such as oxygen, sulfur, or nitrogen; and "perfluoroalkyl group as used herein, refers to a perfluorinated carbon group comprising that may be linear or branched and may comprise 2, 3, 4, 6, 8, 10, 12, 18, or even 20 carbon atoms.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

The present disclosure is directed to a novel monomer and its precursor. These compounds may be used in fluoropolymer polymerizations.

Monomer

The monomer of the present disclosure is shown in Formula I:

$$CX_1X_3{=}CX_2{-}(R_1)_p{-}CZ1Z2\text{-}SO_2M \quad (I)$$

wherein $X_1$, $X_2$, and $X_3$ are independently selected from H, F, Cl, Br, I, $CF_3$, and $CH_3$, and wherein at least one of $X_1$, $X_2$, or $X_3$ is a H; R1 is a linking group; Z1 and Z2 are independently selected from F, Cl, I, Br, $CF_3$, and a perfluoroalkyl group; p is 0 or 1; and M is a cation.

$R_1$ may be non-fluorinated (no hydrogens are replaced by fluorine atoms), partially fluorinated (some of the hydrogens are replaced by fluorine atoms) or perfluorinated (all of the hydrogens are replaced by fluorine atoms). In some embodiments, a hydrogen atom is replaced with a halogen other than fluorine, such as a chlorine, a bromine or an iodine atom, or a combination thereof. $R_1$ may or may not comprise double bonds. $R_1$ may be substituted or unsubstituted, linear or branched, cyclic or acyclic, and may optionally comprise a functional group (e.g., esters, ethers, ketones, amines, halides, etc.).

In one embodiment, $R_1$ is selected from: $—(CH_2)_a—$, $—(CF_2)_a—$, $—(CF_2)_a—O—(CF_2)_b—$, $—(CF_2)_a—[O—(CF_2)_b]_c—$, and $—[(CF_2)_a—O—]_b—[(CF_2)_c—O—]_d$, and combinations thereof, wherein a, b, c, and d are independently at least 1, 2, 3, 4, 10, 20, etc.

In one embodiment, $R_1$ is a perfluorinated group, optionally comprising heteroatoms, and $X_1$, $X_2$, and $X_3$ are all H.

In another embodiment, $R_1$ is a catenary heteroatom such as oxygen, sulfur, or nitrogen.

M in formula I may comprise $H^+$, an inorganic cation including, but not limited to: $Na^+$, $Li^+$, $Cs^+$, $Ca^{+2}$, $K^+$, $NH_4^+$, $Mg^{+2}$, $Zn^{+2}$, and $Cu^{+2}$, and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, and $((CH_3CH_2CH_2CH_2)_4)P^+$.

Exemplary monomers according to formula I include: $CH_2=CH—(CF_2)_4—SO_2H$, $CH_2=CF—(CF_2)_4—SO_2H$, $CH_2=CH—(CF_2)_2—SO_2H$, $CH_2=CH—(CF_2)_6—SO_2H$, $CH_2=CH—CF_2—SO_2H$, $CH_2=CH—(CF_2)_4—SO_2NH_4$, $CH_2=CH—(CF_2)_2—SO_2NH_4$, $CH_2=CH—(CF_2)_6—SO_2NH_4$, $CH_2=CH—CF_2—SO_2NH_4$, $CH_2=CH—(CF_2)_4—SO_2Na$, $CH_2=CH—(CF_2)_2—SO_2Na$, $CH_2=CH—(CF_2)_6—SO_2Na$, $CH_2=CH—CF_2—SO_2Na$, $CH_2=CH—(CF_2)_4—SO_2K$, $CH_2=CH—(CF_2)_2—SO_2K$, $CH_2=CH—(CF_2)_6—SO_2K$, $CH_2=CH—CF_2—SO_2K$, $CH_2=CH—(CF_2)_4—SO_2Li$, $CH_2=CH—(CF_2)_2—SO2Li$, $CH_2=CH—(CF_2)_6—SO_2Li$, $CH_2=CH—CF_2—SO_2Li$, $CH_2=CH—(CF_2)_4—O(CF_2)_2—SO_2H$, $CH_2=CH—(CF_2)_2O(CF_2)_2—SO_2H$, $CH_2=CH—(CF_2)_4—O(CF_2)_2SO_2NH_4$, $CH_2=CH—(CF_2)_2—O(CF_2)_2SO_2NH_4$, $CH_2=CH—(CF_2)_4—O(CF_2)_2SO_2Na$, $CH_2=CH—(CF_2)_2—O(CF_2)_2SO_2Na$, $CH_2=CH—(CF_2)_4—O(CF_2)_2SO_2K$, $CH_2=CH—(CF_2)_2—O(CF_2)_2SO2K$, $CH_2=CH—(CF_2)_4—O(CF_2)_2SO_2Li$, and $CH_2=CH—(CF_2)_2—O(CF_2)_2SO_2Li$.

In one embodiment, the monomer according to formula I includes: $CH_2=CH—(CF_2)_n—SO_2M$ (Ia), where M is a cation and n is at least 1, 2, 4, 6, 10, 20, etc. In another embodiment, the monomer according to formula I includes: $CH_2=CH—(CF_2)_2O(CF_2)_2—SO_2M$ (Ib) where M is defined as above.

In the present disclosure, the monomer according to formula I may be prepared by Method I or Method II as disclosed below.

Precursor

A precursor to the monomer of formula I is shown in formula II:

$$CX_4X_1X_3—CX_5X_2—(R_1)_p—CZ1Z2-SO_2M \quad (II)$$

wherein $X_1$, $X_2$, and $X_3$ are independently selected from H, F, Cl, Br, I, $CF_3$ or $CH_3$, wherein at least one of $X_1$, $X_2$, or $X_3$ is a H, and $X_4$ and $X_5$ are independently selected from H, F, Cl, Br and I; $R_1$ is a linking group; Z1 and Z2 are independently selected from F, Cl, I, Br, $CF_3$, and a perfluoroalkyl group, p is 0 or 1; and M is selected from F and a cation.

$R_1$ may be non-fluorinated, partially fluorinated, or perfluorinated. In some embodiments, the hydrogen atoms are replaced with a halogen other than fluorine, such as a chlorine, a bromine or a iodine atom, or a combination thereof. $R_1$ may or may not comprise double bonds. $R_1$ may be substituted or unsubstituted, linear or branched, cyclic or acyclic, and may optionally comprise a functional group (e.g., esters, ethers, ketones, amines, halides, etc.).

In one embodiment, $R_1$ is a perfluorinated group, optionally comprising a heteroatom, and $X_1$, $X_2$, and $X_3$ are all H.

In another embodiment, $R_1$ is a catenary heteroatom such as oxygen, sulfur, or nitrogen.

M in formula I may comprise F, $H^+$, an inorganic cation including, but not limited to: $Na^+$, $Li^+$, $Cs^+$, $Ca^{+2}$, $K^+$, $NH_4^+$, $Mg^{+2}$, $Zn^{+2}$, and $Cu^{+2}$ and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, and $((CH_3CH_2CH_2CH_2)_4)P^+$.

In one embodiment, the monomer according to formula I includes: $XCH_2CH_2—(CF_2)_n—SO_2M$
(IIa), where M is defined as above; X is selected from H, F, Cl, Br, I, $CF_3$ or $CH_3$; and n is at least 1, 2, 4, 6, 10, 20, etc. In another embodiment, the monomer according to formula I includes: $XCH_2—CH_2—(CF_2)_2O(CF_2)_2—SO_2M$ (IIb) where M is F or a cation and X is selected from F, Cl, Br, and I.

The precursor shown in Formula II is obtained during the process as disclosed in Method II below.

Method I

In Method I, a terminal alkene compound and a halofluorosulfonylfluoride are reacted together to produce a halohydrofluorosulfonylfluoride. The halohydrofluorosulfonylfluoride is then dehalohydrogenated to produce an alkenefluorosulfonylfluoride. Then the alkenefluorosulfonylfluoride is reduced to produce an alkenefluorosulfinic acid or salt. An exemplary reaction scheme is shown below:

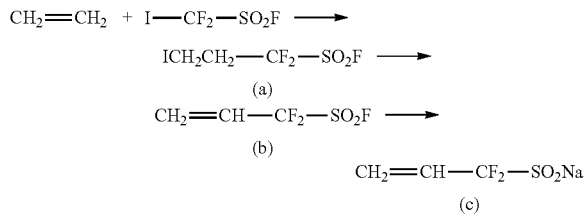

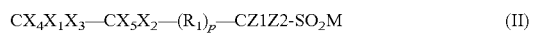

The terminal alkene compound of the present disclosure comprises a terminal carbon-carbon double bond with at least one hydrogen off of the carbon double bond. Exemplary terminal alkene compounds include: ethylene, propylene, butylene, bromoethylene, chloroethylene, fluoroethylene, vinylidene fluoride, $CH_2=CHCl$, $CF_3OCH=CH_2$, $C_3F_7OCH=CH_2$, and $CH_3OCH=CH_2$.

The halofluorosulfonylfluoride of the present disclosure is a ω-halofluorosulfonylfluoride (i.e., a terminal sulfonyl fluoride). The halofluorosulfonylfluoride comprises a compound of the general formula III: $X_5(R_1)_p—CZ1Z2-SO_2F$ (III) where $X_5$ is selected from Br, I, and Cl; $R_1$ is a linking group as described above; Z1 and Z2 are independently selected from F, Cl, Br, $CF_3$ and a perfluoroalkyl group; and p is 0 or 1.

Exemplary halofluorosulfonylfluorides include: $ICF_2CF_2—O—CF_2CF_2SO_2F$, $ICF_2CF_2CF_2CF_2—O—CF_2CF_2SO_2F$, $I(CF_2)_4SO_2F$, $I(CF_2)_3SO_2F$, $I(CF_2)_5SO_2F$, $I(CF_2)_6SO_2F$, $BrCF_2SO_2F$, $BrCF_2CF_2—O—CF_2CF_2SO_2F$, BrCF$_2$CF$_2$CF$_2$CF$_2$—O—CF$_2$CF$_2$SO$_2$F, Br(CF$_2$)$_4$SO$_2$F, Br(CF$_2$)$_3$SO$_2$F, Br(CF$_2$)$_5$SO$_2$F, Br(CF$_2$)$_6$SO$_2$F, ICF$_2$SO$_2$F, and BrCF$_2$SO$_2$F.

In one embodiment, the reaction between the terminal alkene compound and the halofluorosulfonylfluoride is initiated thermally, by photo-irradiation, or in the presence of an initiator, or a combination thereof.

In one embodiment, the reaction between the terminal alkene compound and the halofluorosulfonylfluoride may be conducted at a temperature of between at least 10, 20, 25, 30, or even 35° C.; at most 90, 100, 150, 200 or even 220° C.

In one embodiment, the reaction between the terminal alkene compound and the halofluorosulfonylfluoride may be conducted using photo-irradiation e.g., ultra-violet radiation.

If an initiator is used, exemplary initiators include: a peroxide, a diazo compound, and single electron donor, such as a metal or metal complex, and redox system for radical reaction of fluorinated iodide.

In one embodiment, the reaction between the terminal alkene compound and the halofluorosulfonylfluoride is conducted in the absence of solvent. Eliminating the solvent may reduce processing costs associated with buying and disposing of the solvent.

In one embodiment, the reaction between the terminal alkene compound and the halofluorosulfonylfluoride is conducted in the presence of a first solvent. Exemplary first solvents include: a perfluorinated solvent, such as perfluoromorpholine, and a partially fluorinated solvent, such as C$_4$F$_9$OCH$_3$ and C$_4$F$_9$OCH$_2$CH$_3$.

The ratio of terminal alkene compound to the halofluorosulfonylfluoride to produce the halohydrofluorosulfonylfluoride is at least 1 to 1, or even 2:1. Preferably there is an excess of terminal alkene compound in the addition reaction.

The halohydrofluorosulfonylfluoride produced (e.g., (a) above) is then dehalohydrogenated (loss of a halohydrogen, e.g., HI) to produce an alkenefluorosulfonylfluoride. The alkenefluorosulfonylfluoride comprises a fluorinated carbon group linking a terminal double bond and a terminal sulfonyl fluoride group such as shown in (b).

The dehalohydrogenating may be conducted in the presence of a base. Exemplary bases include: 1,8-diazobicyclo[5,4,0]undec-7-ene (DBU), triethylamine, and tributyl amine. The base should be selected such that the sulfonyl fluoride of the starting material is not hydrolyzed.

In one embodiment, the dehalohydrogenating reaction may be conducted at a temperature of between at least 10, 20, 25, 30, or even 35° C.; at most 60, 70, 80, or even 90° C.

The ratio of base to halohydrofluorosulfonylfluoride is at least 1 to 1, or even 2:1. Preferably there is an excess of base.

In one embodiment, dehalohydrogenating reaction is conducted in the presence of a solvent. Exemplary solvents include, ethers, alcohols, etc.

After dehalohydrogenating the halohydrofluorosulfonylfluoride to form an alkenefluorosulfonylfluoride, the alkenefluorosulfonylfluoride is reduced to produce the monomer according to formula I, an alkenefluorosulfinic acid or salt (e.g., (c) above).

The reducing step may be done in the presence of a reducing agent and a second solvent. The selection of the second solvent may depend on the reducing agent used. Exemplary second solvents include, ethers (such as dialkyl ethers (e.g., diethyl ether), CH$_3$OCH$_2$CH$_2$OCH$_3$, t-butyl methyl ether, glycol dialkyl ether, dioxane, and tetrahydrofuran), alcohols, acetonitrile, water, and combinations thereof.

Hydride reducing agents useful in the present disclosure include those represented by the formula, M'LH$_4$, wherein M' is an alkali metal or an alkaline Earth metal and L is Aluminum or Boron, including, for example, sodium borohydride, sodium cyanoborohydride, potassium borohydride, lithium borohydride, and lithium aluminum hydride. Useful hydride reducing agents also include those represented by the formula, M''H$_n$, wherein M'' is an alkali metal, and n is an integer selected from 1 or 2, including, for example, sodium hydride, lithium hydride, potassium hydride, barium hydride, and calcium hydride. Other useful hydride reducing agents include mono-, di-, or tri(lower alkoxy)alkali metal aluminum hydrides, mono-, di-, or tri-(lower alkoxy lower alkoxy)alkali metal aluminum hydrides, di(lower alkyl) aluminum hydrides, alkalimetalcyanoborohydrides, tri(loweralkyl) tin hydrides, tri(aryl) tin hydrides, Li(C$_2$H$_5$)$_3$BH, and (((CH$_3$)$_2$CHCH$_2$)$_2$AlH)$_2$. Another useful reducing agent is a sulfite such as —CF$_2$SO$_2$F or —CF$_2$SO$_2$M, including K$_2$SO$_3$, Na$_2$SO$_3$, KHSO$_3$ and NaHSO$_3$.

Method II

In Method II, a terminal alkene compound is reacted with a dihalofluorocarbon to produce a haloalkanefluorocarbon halide. The haloalkanefluorocarbon halide is then sulfinated to produce a haloalkenefluorosulfinic acid or salt. Then the haloalkenefluorosulfinic acid or salt is dehalohydrogenated to produce an alkenefluorosulfinic acid or salt. An exemplary reaction scheme is shown below:

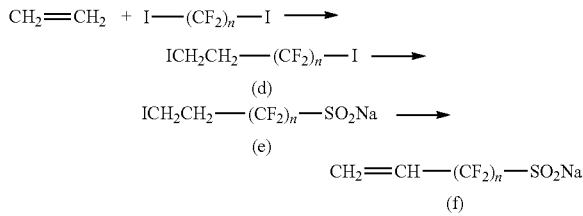

The terminal alkene compound of the present disclosure comprises a terminal carbon-carbon double bond with at least one hydrogen off of the carbon double bond. Exemplary terminal alkene compounds include, ethylene, propylene, butylene, CH$_2$=CHCl, CH$_2$=CCl$_2$, CH$_2$=CHF and CH$_2$=CF$_2$. The dihalofluorocarbon of the present disclosure comprises the general formula IV: X$_6$—(R$_1$)$_p$—CZ1Z2-X$_7$ wherein X$_6$ and X$_7$ are independently selected from Cl, Br, and I; R$_1$ is a linking group as described above; Z1 and Z2 are independently selected from F, Cl, Br, CF$_3$ and a perfluoroalkyl group; p is 0 or 1.

Reacting the terminal alkene compound and the dihalofluorocarbon together produce a haloalkenefluorocarbon halide (e.g., (d) above). The reaction may be conducted at a temperature of between at least 10, 20, 25, 30, or even 35° C.; at most 90, 100, 150, 200 or even 220° C.

In one embodiment, the reaction between the terminal alkene compound and the dihalofluorocarbon is initiated in the presence of an initiator. Initiators as known in the art may be used including peroxides, diazo compounds, metals, and combinations thereof. Exemplary peroxide initiators include: diisobutyryl peroxide (available under the trade designation "TRIGONOX 187-C30" from AkzoNobel, Amsterdam), cumyl peroxyneodecanoate (available under the trade designation "TRIGONOX 99-C75" from AkzoNobel), peroxydicarbonate (available under the trade designation "TRIGONOX ADC" from AkzoNobel), t-butyl peroxyneodecanoate (available under the trade designation "TRIGONOX 23" from AkzoNobel), dibenzoyl peroxide, di-t-butyl peroxide, and t-butyl cumyl peroxide. Exemplary a diazo compound initiators include: 2,2'-Azobis(2-methylbutyronitrile) (available under the trade designation "VAZO 67" from E.I. du Pont de Nemours & Co, Wilmington, Del.) and 2,2'-azobis (isobutyronitrile). Exemplary metal initiators include: Zn, Mg, Ni and Cu or metal complexes such as $Pd(PPh_3)_4$, $Pt(PPh_3)_4$, $Pb(OAc)_4$ and $RhCl(PPh_3)_3$.

The haloalkenefluorocarbon halide produced is then sulfinated to produce the precursor according to formula II, a haloalkenefluorosulfinic acid or salt (see (e) above). In the present disclosure, a sulfinating system is used to dehalosulfinate (i.e., remove a halogen and sulfinate the compound) the haloalkenefluorocarbon halide. Sulfinating systems are known to those skilled in the art. Exemplary sulfinating system include, $Na_2S_2O_4$, $NaHSO_3/(NH_4)_2Ce(NO_3)_6$, $NaHSO_3/FeCl_3$, $NaHSO_3/K_3[Fe(CN)_6]$, $HOCH_2SO_2Na$, and $(NH_2)_2CSO_2$, $Na_2S_2O_5$, and combinations thereof.

The haloalkenefluorosulfinic acid or salt then is dehalohydrogenated to produce the monomer according to formula I, an alkenefluorosulfinic acid or salt (e.g., (f) above).

The dehalohydrogenating may be conducted in the presence of a base. Exemplary bases include: KOH, NaOH, LiOH, $Na_2CO_3$, $NaHCO_3$, $K_2CO_3$, 1,8-diazobicyclo[5,4,0]undec-7-ene (DBU), and combinations thereof.

In one embodiment, the dehalohydrogenating reaction may be conducted at a temperature of between at least 10, 20, 25, 30, or even 35° C.; at most 60, 70, 80, or even 90° C.

The ratio of base to the haloalkenefluorosulfinic acid or salt thereof is at least 1 to 1, or even 2:1. Preferably there is an excess of base.

In one embodiment, dehalohydrogenating reaction is conducted in the presence of a solvent. Exemplary solvents include, water, alcohol, and combinations thereof.

The monomer according to formula I and/or the precursor according formula II may be isolated and purified by known methods. In one embodiment, the crude product is isolated from the reaction mixture by filtration to remove insoluble inorganic salts, then rotary evaporation to remove solvent to give sulfinate salt solid. In another embodiment, the crude solid is purified by extracting with warm alcohol, such as isopropanol to remove insoluble inorganic impurity followed by the stripping out of solvent. In another embodiment, the addition of a concentrated acid, such as, for example, sulfuric acid, is added to protonate the sulfinate salt resulting in a phase split. In another embodiment, the crude product is isolated by the addition of an acid, such as, for example, sulfuric acid, followed by extraction with an organic solvent, such as t-butyl methyl ether and diethyl ether. The desired product in acid form then is isolated by removal of the organic solvent.

In some embodiments further purification of the crude product is sometimes not necessary. The elimination of the purification step may reduce processing time and cost. If desired, the reaction mixture or crude product may be purified, for example, by repeated recrystallization.

The monomer according to formula I may be useful as a surfactant (emulsifier), a dispersion stabilizer, or an initiator. Advantageously, the monomer according to formula I may be useful as an initiator for polymers having fewer undesired end-polar groups, or as a polymerizable surfactant, thus eliminating the need to remove the surfactant post-polymerization.

The monomer of the present disclosure, may be used in polymerizations of fluoropolymers. Because one end of the monomer according to formula I comprises a double bond, the monomer may be used in polymerization reactions. Because the other end of the monomer according to formula I comprises a sulfinic acid or salt thereof, this site is able to form a radical and act as an initiator in polymerization reactions. Therefore, the monomer according to formula I may be consumed during a polymerization. Furthermore, because of the sulfinic acid end group, polymers made using this initiator may have reduced or no amounts of polar end-groups, which may aid in stability of the polymer.

Exemplary embodiments of the present disclosure include:

Embodiment 1

A monomer comprising the composition according to formula I or its precursor, formula II:

  (I)

wherein $X_1$, $X_2$, and $X_3$ are independently selected from H, F, Cl, Br, I, $CF_3$ and $CH_3$, and wherein at least one of $X_1$, $X_2$, or $X_3$ is a H; $R_1$ is a linking group; Z1 and Z2 are independently selected from F, Cl, Br, I, $CF_3$, and a perfluoroalkyl group; p is 0 or 1; and M is a cation; and

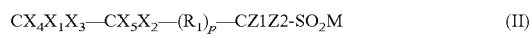  (II)

wherein $X_1$, $X_2$, and $X_3$ are independently selected from H, F, Cl, Br, I, $CF_3$ and $CH_3$, wherein at least one of $X_1$, $X_2$, or $X_3$ is a H, and $X_4$ and $X_5$ are independently selected from H, F, Cl, Br and I; $R_1$ is a linking group; Z1 and Z2 are independently selected from F, Cl, Br, I, $CF_3$, and a perfluoroalkyl group, p is 0 or 1; and M is selected from F, and a cation.

Embodiment 2

The monomer according to embodiment 1, wherein $X_1$, $X_2$, and $X_3$ are all H and $R_1$ is a perfluorinated group.

Embodiment 3

The monomer according to any one of the previous embodiments, wherein $R_1$ is selected from: $-(CH_2)_a-$, $-(CF_2)_a-$, $-(CF_2)_a-O-(CF_2)_b-$, $-(CF_2)_a-[O-(CF_2)_b]_c-$, and $-[(CF_2)_a-O-]$, $-[(CF_2)_c-O-]_d$, and combinations thereof, wherein a, b, c, and d are independently at least 1, 2, 3, 4, 10, 20, etc.

Embodiment 4

The monomer according to any one of the previous embodiments, wherein M is selected from: $H^+$, $Na^+$, $Li^+$, $Cs^+$, $NH_4^+$, and $K^+$.

Embodiment 5

The monomer according to embodiment 1, wherein the composition comprises formula Ia, Ib or their precursors, formula IIa or IIb:

  (Ia); and

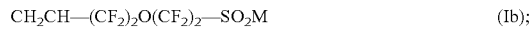  (Ib);

where M is a cation; and

  (IIa); and

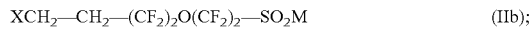  (IIb);

where M is selected from F, and a cation; and X is selected from F, Cl, Br, and I.

Embodiment 6

A method comprising:
(a) reacting a terminal alkene compound with a halofluorosulfonylfluoride to produce a halohydrofluorosulfonylfluoride;
(b) dehalohydrogenating the halohydrofluorosulfonylfluoride to produce an alkenefluorosulfonylfluoride; and
(c) reducing of the alkenefluorosulfonylfluoride to produce an alkenefluorosulfinic acid or salt.

Embodiment 7

The method of embodiment 6 wherein halogen of the halofluorosulfonylfluoride is selected from Br, or I.

Embodiment 8

The method of any one of embodiments 6-7, wherein the reaction of the terminal alkene compound with the halofluorosulfonylfluoride is done at a temperature between 20° C. to 150° C.

Embodiment 9

The method of any one of one of embodiments 6-8, further comprising initiating the reaction of the terminal alkene compound with the halofluorosulfonylfluoride thermally, with photo-irradiation, or in the presence of an initiator.

Embodiment 10

The method of embodiment 9, wherein the initiator is selected from peroxide, diazo compound, metal or metal complex.

Embodiment 11

The method of any one of embodiments 6-10, wherein the terminal alkene compound is at least one of ethylene, $CH_2=CCl_2$, $CH_2=CF_2$, $CH_2=CHF$, $CH_2=CHCl$, and propylene.

Embodiment 12

The method of any one of embodiments 6-11, wherein the halofluorosulfonylfluoride is at least one of $ICF_2CF_2-O-CF_2CF_2SO_2F$, $BrCF_2CF_2-O-CF_2CF_2SO_2F$, $ICF_2CF_2CF_2CF_2-O-CF_2CF_2SO_2F$, $I(CF_2)_4SO_2F$, $I(CF_2)_3SO_2F$, $I(CF_2)_5SO_2F$, $I(CF_2)_6SO_2F$, $Br(CF_2)_4SO_2F$, $Br(CF_2)_3SO_2F$, $Br(CF_2)_5SO_2F$, $Br(CF_2)_6SO_2F$, and $ICF_2SO_2F$.

Embodiment 13

The method of any one of embodiments 6-12, wherein the reaction of the terminal alkene compound with the halofluorosulfonylfluoride is in the absence of solvent.

Embodiment 14

The method of any one of embodiments 6-12, wherein the reaction of the terminal alkene compound with the halofluorosulfonylfluoride is in the presence of first solvent.

Embodiment 15

The method of embodiment 14, wherein the first solvent is selected from at least one of a perfluoromorpholine, $C_4F_9OCH_3$, and $C_4F_9OCH_2CH_3$.

Embodiment 16

The method of any one of embodiments 6-15, wherein the dehalohydrogenating is conducted in the presence of a base.

Embodiment 17

The method of any one of embodiments 6-16, wherein the reducing step comprises a reducing agent in a second solvent.

Embodiment 18

The method of embodiment 17, wherein the second solvent is selected from alcohols and ethers.

Embodiment 20

The method of any one of embodiments 17-18, wherein the reducing agent is selected from: $NH_2NH_2$, sodium borohydride, sodium cyanoborohydride, potassium borohydride, $K_2SO_3$, $Na_2SO_3$, $NaHSO_3$ and $KHSO_3$.

Embodiment 20

A method comprising:
(a) reacting a terminal alkene compound with a dihalofluorocarbon to produce a haloalkenefluorocarbon halide;
(b) sulfinating the haloalkenefluorocarbon halide to produce a haloalkenefluorosulfinic acid or salt; and
(c) dehalohydrogenating the haloalkenefluorosulfinic acid or salt to produce an alkenefluorosulfinic acid or salt.

Embodiment 21

The method of embodiment 20, wherein the terminal alkene compound is reacted with the dihalofluorocarbon in the presence of an initiator.

Embodiment 22

The method of embodiment 21, wherein the initiator is selected from at least one of peroxides, diazo compounds, metals, and combinations thereof.

Embodiment 23

The method of any one of embodiments 20-22, wherein the haloalkenefluorocarbon halide is sulfinated using at least one of $Na_2S_2O_4$, $NaHSO_3/(NH_4)_2Ce(NO_3)_6$, $NaHSO_3/FeCl_3$, $NaHSO_3/K_3-[Fe(CN)_6]$, $HOCH_2SO_2Na$, and $(NH_2)_2CSO_2$, $Na_2S_2O_5$.

Embodiment 24

The method of any one of embodiments 20-23, wherein the terminal alkene compound is selected from at least one of ethylene and propylene.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: bp=boiling point, g=gram, kg=kilograms, min=minutes, mol=mole; cm=centimeter, mm=millimeter, ml=milliliter, L=liter, N=normal, psi=pressure per square inch, MPa=megaPascals, and wt=weight.

| Materials | |
|---|---|
| Material | Source |
| Perfluorinated N-methyl morpholine | Commercially available from VWR |
| $CH_2\!\!=\!\!CH_2$ | Commercially available Sigma-Aldrich Chemical Co. |
| $I\!\!-\!\!CF_2CF_2OCF_2CF_2SO_2F$ | Commercially available from Sigma-Aldrich Chemical Co. |
| DBU | 1,8-diazabicycloundec-7-ene, Commercially available Aldrich |
| THF | Tetrahydrofuran, available from EMD Chemicals Inc. OmniSolv, Gibbstown, NJ |
| $NaBH_4$ | Available from Sigma-Aldrich Chemical Co. |
| $I(CF_2)_4I$ | Available from Shanghai FWD Chemicals Limited, Shanghai 200237, China |
| Initiator | Available under the trade designation "VAZO-67" from E. I. du Pont de Nemours & Co, Wilmington, DE |
| Hexane | Available from EMD Chemicals, Inc. |
| $CH_3CN$ | Available from Sigma-Aldrich Chemical Co. |
| $Na_2S_2O_4$ | Available from J. T. Baker, Avantor Performance Materials, Inc., Phillipsburg, NJ |
| KOH | Available from Sigma-Aldrich Chemical Co. |
| t-BuOMe | t-butyl methyl ether, available from EMD Chemicals, Inc. |

Example 1

Part I

In a 600 mL PARR pressure reactor, commercially available from Parr Instruments Inc., Moline, Ill., 45 g $I\!\!-\!\!CF_2CF_2OCF_2CF_2SO_2F$ (0.10 mol) was reacted with 3.0 g $CH_2\!\!=\!\!CH_2$ (0.107 mol) in the presence of 0.70 g Initiator in 80 g perfluorinated N-methyl morpholine solvent at 67° C. with a pressure of no higher than 75 psi (517 kPa) for 24 hours. $^{19}$F-NMR analysis of the reaction solution indicated that 76% $ICH_2CH_2CF_2CF_2OCF_2\!\!-\!\!SO_2F$ (−120 ppm for —$CH_2CF_2$—, t, J=16.5 Hz) was formed with 24% unreacted $I\!\!-\!\!CF_2CF_2OCF_2CF_2SO_2F$ (−57 ppm for $ICF_2$—). Only the 1/1 adduct was formed. $^{19}$F NMR showed chemical shifts at +43 ppm for —$SO_2F$, −82 and −88 ppm for $CF_2OCF_2$—, −114 ppm for $CF_2SO_2$— and −120 ppm for —$CH_2CF_2$—. Chemical shifts from 1H NMR for $ICH_2CH_2$— were correspondingly at 3.5 (t, 2H) and 2.5 (m, 2H) ppm.

Part II

The crude reaction solution from above containing $ICH_2CH_2CF_2CF_2OCF_2CF_2SO_2F$ was treated with an excess of DBU at room temperature for 4 hours. $^{19}$F NMR analysis showed no effect on the —$SO_2F$ group, and the triplet of $CF_2CH_2$— was changed into doublet×triplet at 121 ppm (Jd=7.8 Hz, Jt=3.6 Hz), indicating the desired reaction occurred to yield $CH_2\!\!=\!\!CHCF_2CF_2OCF_2CF_2SO_2F$. Addition of water to dissolve DBU/HI solid, and the bottom perfluorinated N-methyl morpholine solution was isolated. From F-NMR, no more $I\!\!-\!\!CF_2CF_2OCF_2CF_2SO_2F$ was observed in the isolated solution. The solution was dried over $MgSO_4$. After filtration and rotary evaporation to remove the solvent, 22 g product was obtained (89% isolated yield; bp=115-116° C.). $^{19}$F NMR showed the chemical shifts at +43 ppm (—$SO_2F$), −83.8 ppm (m, —$CF_2O$—), −89.2 ppm (txt, —$CF_2O$—), −114 ppm (dxt, —$CF_2SO_2F$) and 120 ppm (dxt, —$CF_2CH\!\!=\!\!$). Also, $H^1$ NMR confirmed the formation of $CH_2\!\!=\!\!CH$— with chemical shift at 5.7~6.3 ppm (m).

Part III 20 g of $CH_2\!\!=\!\!CH_2CF_2CF_2OCF_2CF_2SO_2F$ from Part II above was dissolved in 20 g THF and put into an additional funnel, which was added dropwise to a dispersion solution of 4.20 g $NaBH_4$ in 70 g THF over the course of 30 minutes at 0° C. under nitrogen while stirring. Then the reaction solution was allowed to warm and was reacted at 20° C. for 4 hours. $^{19}$F NMR showed all $SO_2F$ (+42 ppm) was reacted. The corresponding $CF_2SO_2F$ signal at −114 ppm was not observed and a corresponding new signal of $CF_2SO_2Na$ at −131 ppm was observed in support the formation of $CH_2\!\!=\!\!CHCF_2CF_2OCF_2CF_2SO_2Na$. The extra $NaBH_4$ was removed by reaction with water. Then, the solution was acidified with 2N $H_2SO_4$ aqueous solution to a pH<2. The acidified solution was extracted with t-$BuOCH_3$ (three times with 60 mL each). The combined t-$BuOCH_3$ solution was dried over $MgSO_4$. The solution was then filtered to remove solids and then placed on a rotary evaporator to remove solvent. 15 g product was isolated (corresponding to a 79% yield). $^{19}$F NMR showed chemical shifts of −82 (m) and −87 (m) ppm for $CF_2OCF_2$—, −117 ppm (m) for $CF_2CH\!\!=\!\!$ and −132 for $CF_2SO_2H$. 1H NMR showed chemical shift at 5.73 ppm (dxm, 1H) and 5.82-5.99 ppm (m, 2H) for the corresponding $CH_2\!\!=\!\!CH$— group.

Example 2

Part I

In a 600 mL PARR pressure reactor, 223 g $I(CF_2)_4I$ (MW=454, 0.491 mol) was reacted with 15.4 g $CH_2\!\!=\!\!CH_2$ (MW=28, 0.55 mol, charged in portions) in the presence of 4.58 g Initiator at 60° C. for 24 hours under 60 psi (414 kPa) or less. $^{19}$F NMR analysis of the reaction mixture showed 50% unreacted $I(CF_2)_4I$, 43% $ICH_2CH_2CF_2CF_2CF_2CF_2I$, and 7% $ICH_2CH_2CF_2CF_2CF_2CF_2CH_2CH_2I$. Distillation of the reaction mixture at normal pressure recovered 70 g pure $I(CF_2)_4I$ (31.4%) and 16.5 g of a mixture of $I(CF_2)_4I$ and $ICH_2CH_2CF_2CF_2CF_2CF_2I$ (MW=482). Distillation in vacuum, 79.1 g of $ICH_2CH_2CF_2CF_2CF_2CF_2I$ (MW=482, which equates to about a 33.4% isolated yield) was isolated with boiling point of 88~91° C./7~7.5 mmHg GC (gas chromatography) analysis showed 95% purity. From the remaining solid residue, 12 g $ICH_2CH_2CF_2CF_2CF_2CF_2CH_2CH_2I$ was isolated after purification by recrystallization from hexane (m.p. 96~97° C.). $^{19}$F NMR for $ICH_2CH_2CF_2CF_2CF_2CF_2I$, −57 (m, —$CF_2I$), −111 (m, 2F), −113 (m, 2F), and −121 (t, —$CF_2CH_2$—) ppm.

Part II

Under nitrogen, 50 g of the above distilled $ICH_2CH_2CF_2CF_2CF_2CF_2I$ (MW=482, 95%, 0.1 mol) was treated with 26 g Na$_2$S$_2$O$_4$ (MW=174, 91%, 0.136 mol) and 13 g NaHCO$_3$ (MW=84, 0.154 mol) in 50 g CH$_3$CN and 68 g H$_2$O at room temperature for 2 hours. $^{19}$F NMR showed complete conversion of CF$_2$I (−67 ppm) to form the corresponding CF$_2$SO$_2$Na at ~−130 ppm yielding the desired ICH$_2$CH$_2$(CF$_2$)$_4$SO$_2$Na. The mixture was filtered to remove solids. The filtered solution showed two phases, and only top phase showed fluorinated product based on $^{19}$F NMR analysis. The top phase was separated, and the solvents were removed by rotary evaporation to give 76.5 g wet solid. The wet solid was dissolved in water and the following chemical shifts were recorded, −115 (dxt), −122 (m), −124 (m) and −130 (dxt) ppm. No effect on ICH$_2$CH$_2$— was observed during the dehalosulfination based $^1$H NMR analysis (2.5-3 ppm multiplet for —CH$_2$I and 3.2 ppm (txm) for —CH$_2$CF$_2$—).

Part III

The ICH$_2$CH$_2$(CF$_2$)$_4$SO$_2$Na solid from part II above was dissolved in ethanol and treated with 8.7 g KOH (MW=56, 85%, 0.132 mol) at room temperature, then at 50° C. for 8 hours to precipitate a solid. The reaction mixture was cooled to 20° C. and filtered to remove solids. No significant change in $^{19}$F NMR was observed. The solvent was stripped and the resulting solid was acidified with 2N H$_2$SO$_4$ to a pH<2. The acidified solution was extracted with t-BuOMe (three times, 100 mL each) and the combined ether solution was dried over MgSO$_4$. Finally, the solution was filtered and the solvent was stripped to yield 28 g of the desired semisolid product, CH$_2$=CH(CF$_2$)$_4$SO$_2$H (MW=292), which is soluble in water. The structure of the product was confirmed by NMR analyses, $^{19}$F NMR, −115 (m, =CHCF$_2$—), −122 (txm), −125 (txm) and −130 (t, —CF$_2$SO$_2$H); $^1$H NMR, 4.4~5.6 (m) ppm, indicating no more ICH$_2$CH$_2$— signal. However, ethanol residue was observed in final product, which can be eliminated by fully drying the solid before acidification from a repeated preparation.

Example 3

Part I-a 95 g Br(CF$_2$)$_4$Br (MW=359.8, 0.26 mol) was reacted with CH$_2$=CH$_2$ in the presence of 2.2 g Initiator in a 200 mL PARR pressure reactor at 77° C. for 20 hours under 80 psi. Only 3.4 g CH$_2$=CH$_2$ was charged (MW=28, 0.12 mol). $^{19}$F NMR analysis of the reaction mixture showed 80% unreacted Br(CF$_2$)$_4$Br, 18% desired product, BrCH$_2$CH$_2$CF$_2$CF$_2$CF$_2$CF$_2$Br, and 2% BrCF$_2$CF$_2$CF$_2$CF$_2$H.

Part I-b

Similarly, 95 g Br(CF$_2$)$_4$Br (MW=359.8, 0.26 mol) was reacted with CH$_2$=CH$_2$ in the presence of 2.34 g Luperox TAEC in a 200 mL PARR pressure reactor at 90° C. under 90 psi for 20 hours. Totally 8 g CH$_2$=CH$_2$ was charged (MW=28, 0.33 mol). $^{19}$F NMR analysis of the reaction mixture showed ~56 mol % unreacted BrCF$_2$CF$_2$CF$_2$CF$_2$Br, ~39 mol % Br(CH$_2$CH$_2$)CF$_2$CF$_2$CF$_2$CF$_2$Br (n=1, 2), ~3 mole % BrCH$_2$CH$_2$CF$_2$CF$_2$CF$_2$CF$_2$CH$_2$CH$_2$Br and 2 mole % BrCF$_2$CF$_2$CF$_2$CF$_2$H. Distillation at normal pressure gave 3.5 g mixture of BrCF$_2$CF$_2$CF$_2$CF$_2$H (~20 mol %) and BrCF$_2$CF$_2$CF$_2$CF$_2$Br (80 mol %) at 63~95° C., and 50.7 g recovered BrCF$_2$CF$_2$CF$_2$CF$_2$Br ($^{19}$F NMR, −67 ppm and −120 ppm) at 90-99° C. Distillation in vacuum distillation gave 22.5 g desired product at 60~65° C./9 mmHg (NMR purity 98%), and 12.7 g mixture of Br(CH$_2$CH$_2$)$_2$CF$_2$CF$_2$CF$_2$CF$_2$Br and BrCH$_2$CH$_2$CF$_2$CF$_2$CF$_2$CF$_2$CH$_2$CH$_2$Br with the ratio of around 78 to 22 at 90° C./~0.8 mmHg $^{19}$F NMR for BrCH$_2$CH$_2$CF$_2$CF$_2$CF$_2$CF$_2$Br, −67 (m, —CF$_2$Br), −118 (m, 2F), −121 (m, 2F) and −126 (m, —CF$_2$CH$_2$—) ppm. $^{19}$F NMR for Br(CH$_2$CH$_2$)$_2$CF$_2$CF$_2$$_c$F$_2$CF$_2$Br, −67 (t, —CF$_2$Br), −118 (m, 2F), −120 (m, 2F), and −126 (m, 2F) ppm. $^{19}$F NMR for BrCH$_2$CH$_2$CF$_2$CF$_2$CF$_2$CF$_2$CH$_2$CH$_2$Br, −118 (m, 2F) and −127 (m, 2F) ppm.

Part II

Under nitrogen, 20 g of the above distilled BrCH$_2$CH$_2$CF$_2$CF$_2$CF$_2$CF$_2$Br (MW=386, 0.051 mol) was treated with 12 g Na$_2$S$_2$O$_4$ (MW=174, 91%, 0.062 mol) and 5.3 g NaHCO$_3$ (MW=84, 0.063 mol) in 25 g CH$_3$CN and 25 g H$_2$O at 60° C. for 24 hours. $^{19}$F NMR showed complete conversion of —CF$_2$Br (−67 ppm), and the corresponding —CF$_2$SO$_2$M signal at −130 ppm was appeared, indicating the formation of the desired BrCH$_2$CH$_2$(CF$_2$)$_4$SO$_2$Na. The mixture was filtered to remove solids, and the solvents were removed by rotary evaporation to give 28 g wet solid, which was directly used for next HBr-elimination reaction Part III The above BrCH$_2$CH$_2$(CF$_2$)$_4$SO$_2$Na solid was dissolved in 50 g ethanol and treated with 6.6 g KOH (MW=56, 85%, 0.10 mol) at room temperature, then at 55° C. for 2 hours to precipitate a solid. After the reaction mixture was cooled to 20° C., the mixture was filtered to remove solids. The solvent was stripped and the resulting solid was acidified with 2N H$_2$SO$_4$ to pH<2. The acidified solution was extracted with t-BuOMe (3×60 mL) and the combined ether solution was dried over MgSO$_4$. Finally, the dried solution was filtered and the solvent was stripped to yield 13.0 g of the desired semisolid product, CH$_2$=CH(CF$_2$)$_4$SO$_2$H (MW=292, ~95% purity based on NMR analysis and ~82% isolated yield based on BrCH$_2$CH$_2$CF$_2$CF$_2$CF$_2$CF$_2$Br), which is soluble in water. The structure of the product was confirmed by $^{19}$F and $^1$H NMR analyses.

Foreseeable modifications and alterations of this invention will be apparent to those skilled in the art without departing from the scope and spirit of this invention. This invention should not be restricted to the embodiments that are set forth in this application for illustrative purposes.

What is claimed is:
1. A monomer according to formula I:

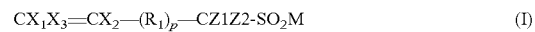

(I)

wherein $X_1$, $X_2$, and $X_3$ are independently selected from H, F, Cl, Br, I, CF$_3$ and CH$_3$, and wherein at least one of $X_1$, $X_2$, or $X_3$ is a H; $R_1$ is a linking group; Z1 and Z2 are independently selected from F, Cl, Br, I, CF$_3$, and a perfluoroalkyl group; p is 0 or 1; and M is a cation.

2. The monomer according to claim 1, wherein $X_1$, $X_2$, and $X_3$ are all H and $R_1$ is a perfluorinated group.

3. The monomer according to claim 1, wherein $R_1$ is selected from: —(CH$_2$)$_a$—, —(CF$_2$)$_a$—, —(CF$_2$)$_a$—O—(CF$_2$)$_b$—, —(CF$_2$)$_a$—[O—(CF$_2$)$_b$]$_c$—, and —[(CF$_2$)$_a$—O—]$_b$—[(CF$_2$)$_c$—O—]$_d$, and combinations thereof, wherein a, b, c, and d are independently at least 1, 2, 3, 4, 10, 20, etc.

4. The monomer according to claim 1, wherein the monomer is selected from formula Ia or Ib:

$$CH_2=CH-(CF_2)_4-SO_2M \quad \text{(Ia); and}$$

$$CH_2=CH-(CF_2)_2O(CF_2)_2-SO_2M \quad \text{(Ib);}$$

where M is a cation.

5. The monomer according to claim 1, wherein M is selected from: $H^+$, $Na^+$, $Li^+$, $Cs^+$, $NH_4^+$, and $K^+$.

* * * * *

UNITED STATES PATENT AND TRADEMARK OFFICE
CERTIFICATE OF CORRECTION

PATENT NO. : 9,187,416 B2
APPLICATION NO. : 13/885202
DATED : November 17, 2015
INVENTOR(S) : Qiu et al.

It is certified that error appears in the above-identified patent and that said Letters Patent is hereby corrected as shown below:

Column 3,
Lines 34-35, delete "$CH_2$—CH" and insert -- $CH_2$=CH --, therefor.
Line 35, delete "$CH_2$—CH" and insert -- $CH_2$=CH --, therefor.
Lines 35-36, delete "$CH_2$—CH" and insert -- $CH_2$=CH --, therefor.
Line 39, delete both instances of "$CH_2$—CH" and insert -- $CH_2$=CH --, therefor.
Line 40, delete both instances of "$CH_2$—CH" and insert -- $CH_2$=CH --, therefor.
Line 41, delete "$CH_2$—CH" and insert -- $CH_2$=CH --, therefor.
Line 42, delete "$CH_2$—CH" and insert -- $CH_2$=CH --, therefor.
Line 43, delete both instances of "$CH_2$—CH" and insert -- $CH_2$=CH --, therefor.
Line 44, delete "$CH_2$—CH" and insert -- $CH_2$=CH --, therefor.
Line 45, delete all instances of "$CH_2$—CH" and insert -- $CH_2$=CH --, therefor.

Column 8,
Line 40, delete "—$[(CF_2)a$—O—$]$,—$[(CF_2)_c$—O—$]_d$," and insert
-- —$[(CF_2)a$—O—$]_b$—$[(CF_2)_c$—O—$]_d$, --, therefor.
Line 59, delete "$CH_2CH$" and insert -- $CH_2$=CH --, therefor.

Column 10,
Line 22, delete "Embodiment 20" and insert -- Embodiment 19 --, therefor.
Line 55, delete "$NaHSO_3/K_3$—$[Fe(CN)_6]$," and insert -- $NaHSO_3/K_3[Fe(CN)_6]$, --, therefor.

Signed and Sealed this
Seventeenth Day of May, 2016

Michelle K. Lee
*Director of the United States Patent and Trademark Office*